United States Patent [19]

Sunshine et al.

[11] 4,420,483
[45] Dec. 13, 1983

[54] ANALGESIC AND ANTI-INFLAMMATORY COMPOSITIONS COMPRISING IBUPROFEN AND METHODS OF USING SAME

[75] Inventors: Abraham Sunshine, New York; Eugene M. Laska, Larchmont; Carole E. Siegel, Mamaroneck, all of N.Y.

[73] Assignee: Richardson-Vicks, Inc., Wilton, Conn.

[21] Appl. No.: 400,645

[22] Filed: Jul. 22, 1982

[51] Int. Cl.³ .................. A61K 31/19; A61K 31/53
[52] U.S. Cl. ................................. 424/253; 424/317
[58] Field of Search .......................... 424/253, 317

[56] References Cited

PUBLICATIONS

Chem. Abst., 96:149162u, (1982).

Primary Examiner—Stanley J. Friedman
Attorney, Agent, or Firm—Burns, Doane, Swecker & Mathis

[57] ABSTRACT

Novel analgesic and anti-inflammatory compositions of matter for use in eliciting an analgesic or anti-inflammatory response, said compositions comprising ibuprofen and caffeine, are disclosed. When used in combination with ibuprofen, caffeine enhances the analgesic or anti-inflammatory response and also hastens its onset.

22 Claims, No Drawings

ANALGESIC AND ANTI-INFLAMMATORY COMPOSITIONS COMPRISING IBUPROFEN AND METHODS OF USING SAME

CROSS-REFERENCE TO RELATED APPLICATIONS

The subject matter of this application is related to that of our patent applications entitled "IMPROVED ANALGESIC COMPOSITIONS COMPRISING PROPIRAM AND METHODS OF USING SAME" and "IMPROVED ANALGESIC AND ANTI-INFLAMMATORY COMPOSITIONS COMPRISING CAFFEINE AND METHODS OF USING SAME", filed concurrently herewith, both incorporated by reference herein and relied upon.

FIELD OF THE INVENTION

The present invention relates to novel pharmaceutical compositions of matter comprising ibuprofen and caffeine, and to methods of using said compositions to hasten the onset of an analgesic or anti-inflammatory response and to enhance an analgesic or anti-inflammatory response.

BACKGROUND ART

Ibuprofen, or ($\pm$) 2-(p-isobutylphenyl)propionic acid, has the structural formula

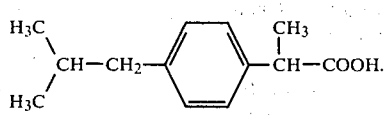

The compound is well-known as a nonsteroidal anti-inflammatory drug having analgesic and antipyretic activity; it is peripherally acting and inhibits prostaglandin synthesis. Ibuprofen is currently marketed in the United States as Motrin ®, which is available in 300, 400 and 600 mg tablets for oral administration. For the treatment of mild to moderate pain, 400 mg every 4 to 6 hours, not to exceed 2400 mg total daily dose, is generally recommended. For the treatment of acute flareups and long-term management of rheumatoid arthritis and and osteoarthritis, 300 mg, 400 mg or 600 mg three or four times a day is recommended. See also *Physician's Desk Reference*, 35th edition, 1981, pp. 1831–1833.

Caffeine, or 3,7-dihydro-1,3,7-trimethyl-1H-purine-2,6-dione, has the structural formula

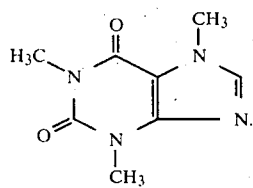

This substance has been used alone, intravenously, in the treatment of headaches and has also been used in combination with selected drugs. Compositions containing one or more of the analgesics aspirin, acetaminophen and phenacetin in combination with varying amounts of caffeine have been marketed in the past; examples of these combinations include the products known commercially as Excedrin ®, Anacin ® and A.P.C. The nonsteroidal analgesic components of these mixtures have the following structural formulas:

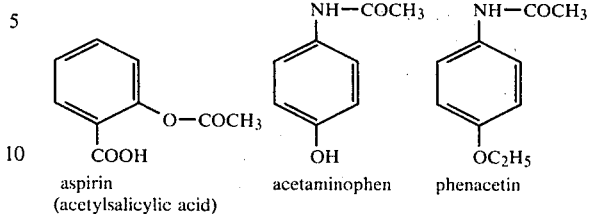

aspirin (acetylsalicylic acid)   acetaminophen   phenacetin

Many workers have sought to demonstrate the efficacy of such caffeine/analgesic combination products. An extensive review of the literature on caffeine and analgesics has been published ["Over-The-Counter Drugs: Establishment of a Monograph for OTC Internal Analgesic, Antipyretic and Antirheumatic Products," *Federal Register*, 1977, 42 (131):35482–35485] and several relevant additional articles have appeared. Most animal studies on caffeine analgesia have been performed on the rat. Williams (*Toxicology and Applied Pharmacology*, 1959, 1:447–453) utilized experimental pain and found that caffeine alone exerted analgesic effects on rats and when combined with aspirin; the effect appeared additive but not potentiating. Vinegar et al (*Proceedings of the Society for Experimental Biology and Medicine*, 1976, 151:556–560), ten years later, found that in the rat caffeine potentiates the acute anti-inflammatory and analgesic activity of aspirin. Siegers (*Pharmacology*, 1973, 10:19–27) studied the effect of oral doses of caffeine (10, 50 and 100 mg/kg) given to rats together with acetaminophen and found that caffeine inhibited its absorption and lowered its serum concentration. He suggested that delayed stomach emptying as a result of the relaxing effect of caffeine on gastric smooth muscle was probably the cause of the diminished absorption of orally administered drugs in the presence of caffeine. Despite this finding, acetaminophen analgesia was not decreased by caffeine. In agreement with Williams and Vinegar and his associates, Siegers found that caffeine itself had analgesic activity. Only in the lowest dose of caffeine studied, a dose at which analgesia was not exhibited, was there a reduction in the acetaminophen induced analgesia. In a more recent paper, Seegers et al (*Arch. Int. Pharmacodyn.*, 1981, 251:237–254) demonstrated an anti-inflammatory, analgesic effect of caffeine in rats. He also found that the combination of caffeine, aspirin and acetaminophen as well as the combination of caffeine, aspirin and phenacetin at low doses produced anti-inflammatory, analgesic effects which are at least as great as would be expected on the basis of addition, while at high doses, the results suggested potentiation. Citing the work of Giertz and Jurna (*Naturwissenschaften*, 1957, 44:445), and Fuchs and Giertz (*Arzneimittelforsch*, 1960, 10:526–530), who observed that caffeine induced analgesia in assays in mice in which inflammation was not involved, Seegers asserted that, "it seems safe to assume that the analgesic activity of caffeine consists of at least two components, one independent of and another one dependent on its anti-inflammatory activity."

The earliest relevant study in humans was reported by Wallenstein (*Proceedings of the aspirin symposium*, held at the Royal College of Surgeons, London, 1975). Two tablets of a combination in which each tablet contained aspirin 210 mg, acetaminophen 150 mg and caffeine 30 mg, clearly and significantly produced more analgesia than the combination without caffeine. The one tablet dose of the combination had higher mean scores than either component alone, but was not superior to the combination without caffeine. Wallenstein speculated that, "dosage may be an important factor, and caffeine may simply be ineffective much below the 60 mg dose". Booy (*Nederlands Tijdschrift Voor Tandheelkinde*, 1972, 79:69–75) studied pain relief on each of two days after tooth extraction. Patients who reported "great pain" on the first day obtained more pain relief from 1000 mg of acetaminophen plus 100 mg of caffeine than from 1000 mg of acetaminophen alone. On the second day this difference was not found, although on both days all treatments were superior to placebo. Lim et al (*Clin. Pharmacol. Ther.*, 1967, 8:521–542), reporting a study in which experimental pain was induced in the subjects by bradykinin, observed that the combination of aspirin 520 mg and acetaminophen 260 mg given orally could not be distinguished from placebo, whereas the same combination in lesser quantities, aspirin 325 mg and acetaminophen 162.5 mg plus caffeine 32.5 mg was significantly different from placebo at 15, 60, 75, 105, and 120 minutes after taking the drug. A double-blind, crossover study of 216 patients by Wojcicki et al [*Archivum Immunologiae et Therapeae Experimentalis*, 1977, 25(2):175–179] compared the activity of 1000 mg of acetaminophen plus 100 mg of caffeine against the same quantity of acetaminophen alone. One group of patients in the trial were suffering severe and frequently occurring idiopathic headache and a second group had moderate post-operative orthopedic pain. The authors concluded that the relief of pain was far greater with the caffeine combination than with acetaminophen alone or with aspirin alone. Jain et al (*Clin. Pharmacol. Ther.*, 1978,24:69–75) first studied 70 postpartum patients with moderate to severe uterine cramp and/or episiotomy pain and then a second group of 70 patients limited to severe pain only. Comparing 800 mg aspirin plus 64 mg of caffeine to 650 mg aspirin alone, these authors concluded that in patients with severe episiotomy pain the combination is the more effective analgesic.

Caffeine use in the treatment of headache has a long history. The FDA Advisory Panel, in its review of caffeine [*Federal Register*, 1977, 42 (131):35482–35485] argued that the known biochemical effect of caffeine on small blood vessels provides a plausible explanation for its effectiveness in treating headache associated with cerebral blood vessels. Recently Sechzer [*Curr. Therapy Research*, 1979, 26(4)] found that the intravenous administration of caffeine sodium benzoate rapidly provided relief in the majority of patients experiencing headache resulting from dural puncture or spinal anesthesia. The author, referring to the literature on the mechanism of action of caffeine on cerebral blood flow and on cerebral vascular tone, argues from the opposite perspective of the Panel that the analgesic relief obtained implies that an intracranial vascular component is the primary factor in such headaches.

Changes in mood and over-all sense of "well-being" after administration of caffeine have been widely reported in the literature. Beginning in the early part of this century, Hollingsworth (*Arch. Psychol.*, 1912, 22:1) reported beneficial motor and mental effects from 65 to 130 mg of caffeine, and tremor, poor motor performance, and insomnia caused by 390 mg of caffeine. Many studies over the past 70 years have confirmed those findings. Review articles on the xanthines [Ritchie, J. M. "Central nervous system stimulants. 2. The xanthines," Goodman, L. S. & Gilman, A. (Eds.), *The pharmacological basis of therapeutics*, 4th Ed., New York: Macmillan Co., 1970; Stephenson, P. E., "Physiologic and psychotropic effects of caffeine on man," [*J. Amer. Diet. Assoc.*, 1977, 71(3):240–247] report that doses of 50 to 200 mg of caffeine result in increased alertness, decreased drowsiness, and lessened fatigue. Doses in the range of 200 to 500 mg may produce headaches, tremor, nervousness and irritability.

After extensively reviewing the relevant literature, the most significant contributions of which are summarized above, the FDA Advisory Panel in 1977 concluded that caffeine when used as an analgesic adjuvant was safe, but that there was insufficient data to demonstrate that caffeine contributes anything to the action of the analgesic [*Federal Register*, 1977, 42 (131):35482–35485]. The Panel stated:

> Unfortunately, the information and data submitted, fail to demonstrate conclusively that caffeine in combination is effective as an analgesic, antipyretic and/or antirheumatic ingredient. The Panel finds there is little evidence to show that this ingredient even contributes to these pharmacological effects in the clinical situation.

This remains the official position on the question up to the present time. Consequently, many of the analgesic/caffeine combination products previously available are no longer on the market.

SUMMARY OF THE INVENTION

Surprisingly, the present inventors now find that ibuprofen, which differs substantially in chemical structure from aspirin, phenacetin and acetaminophen, and which has a significantly different biological profile therefrom, can be advantageously formulated into a novel pharmaceutical composition together with caffeine and administered to mammals, especially humans, to not only elicit a more potent analgesic or anti-inflammatory response but also to evoke such response more rapidly than possible by administration of ibuprofen alone.

In one aspect, the present invention thus provides a novel pharmaceutical composition of matter for use in eliciting an analgesic or anti-inflammatory response, said composition comprising an effective analgesic or anti-inflammatory amount of ibuprofen and an amount of caffeine sufficient to hasten the onset of the analgesic or anti-inflammatory response or to enhance the analgesic or anti-inflammatory response. Typically, the active ingredients are further associated with a nontoxic pharmaceutically acceptable inert carrier therefor.

In another aspect, the present invention provides a method of hastening the onset of analgesia or of an anti-inflammatory response in a mammal resulting from administration of an effective analgesic or anti-inflammatory amount of ibuprofen, said method comprising administering to said mammal said effective analgesic or anti-inflammatory amount of ibuprofen together with an amount of caffeine sufficient to hasten the onset of analgesia or of the anti-inflammatory response.

In yet another aspect, the present invention provides a method of eliciting an enhanced analgesic or anti-inflammatory response in a mammal, said method comprising administering to said mammal an effective analgesic or anti-inflammatory amount of ibuprofen together with an amount of caffeine sufficient to enhance the analgesic or anti-inflammatory response.

DETAILED DESCRIPTION OF THE INVENTION

The term "caffeine" as used herein is intended to encompass not only caffeine as the anhydrous powder, but any salt or derivative of caffeine or any compounded mixture thereof which is nontoxic, pharamaceutically acceptable and which is capable of hastening and enhancing an analgesic or anti-inflammatory response when combined with ibuprofen. See, for example, *The Merck Index*, ninth edition, Merck & Co., Rahway, New Jersey (1976), pp. 207–208, for a description of caffeine salts, derivatives and mixtures which may prove useful in the compositions of the present invention. Nevertheless, caffeine as the anhydrous powder base is presently preferred and, where specific amounts of caffeine are set forth below, such amounts are given in mg of the anhydrous base.

The term "ibuprofen" as used herein is intended to encompass not only 2-(p-isobutylphenyl)propionic acid itself but also any pharmaceutically acceptable salt thereof, e.g. ibuprofen aluminum (*Chemical Abstracts Registry No.* 61054-06-6). However, where specific amounts of ibuprofen are set forth below, such amounts are given in mg of the acid unless otherwise specified.

Ibuprofen, when combined with caffeine in accord with the present invention, produces the following unexpected results:

(1) the analgesic or anti-inflammatory effect of ibuprofen on the mammal is brought on more quickly;
(2) lower amounts of ibuprofen are required for the same analgesic or anti-inflammatory effect; and
(3) across all doses, a greater analgesic or anti-inflammatory response is achieved.

For patients suffering pain, the time from administration of medication to the onset of effective relief is clearly of paramount importance. The present inventors' discovery that caffeine substantially shortens the onset time, (i.e. substantially hastens the onset) of analgesia is therefore very significant; moreover, it is completely unexpected. Likewise, in patients suffering from rheumatoid arthritis or osteoarthritis, the substantial shortening of onset time provided by this invention is extremely important, not only because it provides faster relief from pain but also because it provides more rapid relief from other aspects of the inflammatory disease, e.g. morning stiffness.

Further, the ability of caffeine to enhance analgesia or to enhance the anti-inflammatory response, i.e. to substantially reduce the amount of ibuprofen which is required to elicit a given analgesic or anti-inflammatory reponse, is also an unexpected and very important aspect of this invention. This unexpected and important finding permits the use of ibuprofen in quantities substantially less than the dosages presently suggested as an analgesic or anti-inflammatory agent in humans. Use of lower doses should in turn lower the incidence and/or severity of undesirable side effects. Moreover, at a given dosage level, a greater analgesic response can be achieved.

More specifically, it is believed that onset time for analgesia or for the anti-inflammatory response can be reached, on the average, about one-fourth to about one-third sooner when a composition of the invention is used rather than when ibuprofen alone is employed. Also, approximately one-fifth to one-third less ibuprofen can be used in the caffeine combination to achieve the same analgesic or anti-inflammatory effect as that obtained by use of ibuprofen alone; in other words, the addition of caffeine decreases the amount of ibuprofen needed to two-thirds to four-fifths of the usual amount to achieve the same effect. These ratios may vary, however, depending on the patient's individual response, the selected dosage level of the active ingredient etc.

The precise amount of ibuprofen for use in the present compositions will vary depending, for example, on the size and kind of the mammal and the condition for which the drug is administered. For use in humans, the analgesically effective amount of ibuprofen in a unit dose composition will typically be from about 50 to 400 mg, although greater amounts may be employed if desired. The amount of caffeine in the analgesic composition will be an amount sufficient to shorten the onset time and/or to enhance analgesia. For humans, a unit dosage analgesic composition will typically contain from about 60 to about 200 mg caffeine; this dosage level of caffeine is generally sufficient to both shorten the onset time and enhance analgesia. The daily analgesic dose in humans preferably will not exceed 2400 mg ibuprofen and 1000 mg caffeine, although greater amounts could be employed if tolerated by the patient.

Preferred unit dosage compositions for use in the treatment of mild to moderate pain include:

about 50 to 150 mg ibuprofen + about 100 to 150 mg caffeine;

about 175 to 250 mg ibuprofen + about 100 to 150 mg caffeine; and about 300 to 400 mg ibuprofen + about 100 to 150 mg caffeine.

For use in humans, the effective anti-inflammatory amount of ibuprofen in a unit dose composition will typically be from about 50 to 600 mg, although greater amounts may be employed if desired. The amount of caffeine in the anti-inflammatory composition will be an amount sufficient to shorten the onset time and/or to enhance the anti-inflammatory response. For humans, a unit dosage anti-inflammatory composition will typically contain from about 60 to 200 mg caffeine; this dosage level of caffeine is generally sufficient to both shorten the onset time and enhance the anti-inflammatory response. The daily anti-inflammatory dose in humans preferably will not exceed 3000 mg ibuprofen and 1000 mg caffeine, although greater amounts could be employed if tolerated by the patient. Preferred unit dosage compositions for use in the treatment of inflammation include about 50 to 150 mg ibuprofen + about 60 to 150 mg caffeine; about 175 to 250 mg ibuprofen + about 60 to 150 mg caffeine; about 300 to 400 mg ibuprofen + about 60 to 150 mg caffeine; and about 450 to 600 mg ibuprofen + about 60 to 150 mg caffeine.

While the compositions of the invention are preferably for oral use, they may also be formulated for and administered by other methods which are known for administering non-narcotic analgesics/nonsteroidal anti-inflammatory drugs, e.g. as suppositories. Also, the preferred human dosage levels indicated above are for use in adults; pediatric compositions would contain proportionately less of the active ingredients.

The compositions of the present invention are very conveniently administered to mammals by any route of administration suitable for ibuprofen itself, e.g. oral or rectal. Preferably, the ibuprofen/caffeine combination is formulated with any suitable nontoxic pharmaceutically acceptable inert carrier material. Such carrier materials are well known to those skilled in the art of pharmaceutical formulations. For those not skilled in the art, reference is made to the text entitled, "REMINGTON'S PHARMACEUTICAL SCIENCES" (Fourteenth Edition), 1970. In a typical preparation for oral administration, e.g., tablet or capsule, ibuprofen in an effective analgesic or anti-inflammatory amount and caffeine in an amount sufficient to hasten the onset of the analgesic or anti-inflammatory response, or caffeine in an amount sufficient to enhance the analgesic or anti-inflammatory response, are combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, betonite, cellulose, wood products, alginic acid, guar gum, citris pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. Such compositions should preferably contain at least 0.1% of active components; generally, the active ingredients will be between about 2% to about 60% of the weight of the unit. Typical unit dosage forms for oral administration will contain 50 to 600 mg ibuprofen and 60 to 200 mg caffeine, preferably 50 to 400 mg ibuprofen and 60 to 150 mg caffeine. Illustrative of typical unit dosage forms are tablets or capsules containing:

50 mg ibuprofen + 65 mg caffeine or 130 mg caffeine;
100 mg ibuprofen + 65 mg caffeine or 130 mg caffeine;
200 mg ibuprofen + 65 mg caffeine or 130 mg caffeine;
300 mg ibuprofen + 65 mg caffeine or 130 mg caffeine;
400 mg ibuprofen + 65 mg caffeine or 130 mg caffeine;
500 mg ibuprofen + 65 mg caffeine or 130 mg caffeine; and
600 mg ibuprofen + 65 caffeine or 130 mg caffeine.

The above examples are typical when both active ingredients are formulated for immediate release. If one or both of the active components is/are formulated for sustained release, much larger amounts would of course be incorporated in an individual unit.

The analgesic and anti-inflammatory effects of the compositions of the present invention can be quantitatively evaluated in animals in the tests described below:

Antiphenylquinone Writhing Test

This test is a standard procedure for detecting and comparing analgesic activity and generally correlates well with human efficacy.

Mice are first dosed with the medications studied. The medications used are two dose levels of ibuprofen with and without caffeine. The mice are then challenged with phenyl-p-benzoquinone given intraperitoneally and observed for the characteristic stretch-writhing syndrome. Lack of writhing constitutes a positive response. The degree of analgesic protection can be calculated on the basis of suppression of writhing relative to control animals run the same day. Time response data are also obtained. The test is a modification from the methods of Sigmund et al and Blumberg et al (Sigmund, E., Cadmus, R., and Lu, G., *Proc. Soc. Exp. Biol. and Med.* 95, 729–731, 1957; Blumberg, H. et al., *Proc. Soc. Exp. Biol. and Med.* 118, 763–766, 1965).

The Inflamed Rat Paw Test

Pressure Induced Stimuli

The method of Randall-Selitto, modified according to Winter et al is used to ascertain the escape response threshold resulting from the application of increasing pressure to the yeast inflamed left hind paw. Drug treatment is given. The medications studied are two dose levels of ibuprofen with and without caffeine. A constantly increasing force is applied to the paw and the "flight reaction" is observed and recorded (Randall, L. Q., and Selitto, J. J.: *Arch. Int. Pharmacodyn.*, II, 409–419, 1957; Winter, C. A., and Lars, F.: *J. Pharmacol. Exp. Therap.*, 148, 373–379, 1965).

Adjuvant Arthritis Test

Adjuvant arthritis in the rat is a widely used model for human rheumatoid arthritis. It is basically an immunological reaction, involving a cellular immune response to an injected bacterial adjuvant. The response is systemic, but develops mainly in the limbs as a polyarthritis. The degree of arthritis in the hind legs is assessed either visually or by measuring the foot volume on the 21st day after injection of the adjuvant.

A single subcutaneous injection of 1 mg *Mycobacterium butyricum* suspended in 0.1 ml mineral oil is injected into the right hindpaws of rats. The swelling of the injected hind leg measured on day 16 constitutes the secondary response. Drugs are administered p.o. daily, beginning 1 day prior to injection of adjuvant. The medications used are two dose levels of ibuprofen with and without caffeine. Results are expressed as percent suppression of the control. [Walz, D. T., Di Martino, M. J., and Misher, A.: *Ann. Rheum. Dis.*, 30, 303–306 (1971)].

To establish the efficacy of the composition of this invention in humans, patients with moderate to severe pain requiring an oral analgesic or patients suffering from inflammatory or degenerative joint disease, e.g. rheumatoid arthritis, osteoarthritis, gout or acute musculo-skeletal disease requiring an oral anti-inflammatory agent, can be administered ibuprofen with and without caffeine. To determine analgesic efficacy, a nurse observer interviews the patients as to their level of pain or stiffness and swelling at subsequent periods of time. Patients are asked to subjectively estimate the time at which the medication begins to provide relief. Appropriate statistical methods can be used to show that on the average the analgesic or anti-inflammatory agent with caffeine has shorter onset and is more efficacious. (Laska, E., Gormely, M., Sushine, A., Belleville, J. W., Kantor, T., Forrest, W. H., Siegel, C., and Meisner, M.: "A Bioassay Computer Program for Analgesic Clinical Trials", *Clin. Pharmacol. Ther.* 8:658, 1967; Cox, D. R., "Regression Models and Life Tables", *Journal Royal Statistical Society*, Series B, Volume 34:187–202, 1972). Evaluation of efficacy in inflammatory and degenerative joint disease is accomplished by patient's self-assessment of severity of pain, duration of morning stiffness, general feeling, and ease of movement; and by physician's evaluation of objective measures such as tenderness, swelling, number of painful joints, plus various tests of function such as grip strength, speed of walking, chest expansion and finger to floor.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be, within the full range of equivalence of the following claims.

What we claim is:

1. The method of eliciting an onset hastened and enhanced analgesic and anti-inflammatory response in a mammalian organism in need of such treatment, comprising administering to such organism a unit dosage analgesically and anti-inflammatorily effective amount of a pharmaceuticl composition of matter comprising an ibuprofen component and an ibuprofen potentiating adjuvant therefor, said adjuvant consisting essentially of ibuprofen and anti-inflammatory onset hastening and enhancing amount of caffeine.

2. The method as defined by claim 1, comprising administering to such organism from about 50 to about 400 mg ibuprofen together with from about 60 to about 200 mg caffeine.

3. The method as defined by claim 2, comprising administering to such organism from about 50 to about 150 mg ibuprofen together with from about 65 to about 150 mg caffeine.

4. The method as defined by claim 2, comprising administering to such organsim from about 175 to about 250 mg ibuprofen together with from about 65 to about 150 mg caffeine.

5. The method as defined by claim 2, comprising administering to such organism from about 300 to about 400 mg ibuprofen together with from about 100 to 150 mg caffeine.

6. The method as defined by claim 1, comprising administering to such organism from about 50 to about 600 mg ibuprofen together with from about 60 to about 200 mg caffeine.

7. The method as defined by claim 1, comprising administering to such organism from about 450 to about 600 mg ibuprofen together with from about 100 to about 150 mg caffeine.

8. A pharmaceutical composition of matter adapted to elicit an onset hastened and enhanced analgesic and anti-inflammatory response in a mammalian organism in need of such treatment, said composition comprising a unit dosage analgesically and anti-inflammatorily effective amount of an ibuprofen component and an ibuprofen potentiating adjuvant therefor, said adjuvant consisting essentially of ibuprofen and anti-inflammatory onset hastening and enhancing amount of caffeine.

9. The pharmaceutical composition of matter as defined by claim 8, comprising from about 50 to about 400 mg ibuprofen.

10. The pharmaceutical composition as defined by claim 8, said adjuvant consisting essentially of from about 60 to about 200 mg caffeine.

11. The pharmaceutical composition of matter as defined by claim 10, comprising from about 50 to about 400 mg ibuprofen.

12. The pharmaceutical composition of matter as defined by claim 11, comprising from about 50 to about 150 mg ibuprofen and said adjuvant consisting essentially of from about 65 to about 150 mg caffeine.

13. The pharmaceutical composition of matter as defined by claim 11, comprising from about 175 to about 250 mg ibuprofen and said adjuvant consisting essentially of from about 65 to about 150 mg caffeine.

14. The pharmaceutical composition of matter as defined by claim 11, comprising from about 300 to about 400 mg ibuprofen and said adjuvant consisting essentially of from about 100 to about 150 mg caffeine.

15. The pharmaceutical composition of matter as defined by claim 8, further comprising a nontoxic pharmaceutically acceptable inert carrier.

16. The pharmaceutical composition of matter as defined by claim 15, said composition being adapted for oral administration.

17. The pharmaceutical composition of matter as defined by claim 16, said composition being formulated as a tablet or capsule.

18. The pharmaceutical composition of matter as defined by claim 16, said composition being adapted for rectal administration.

19. The pharmaceutical composition of matter as defined by claim 18, said composition being formulated as a suppository.

20. The pharmaceutical composition of matter as defined by claim 8, comprising from about 50 to about 600 mg ibuprofen.

21. The pharmaceutical composition of matter as defined by claim 20, said adjuvant consisting essentially of from about 60 to about 200 mg caffeine.

22. The pharmaceutical composition of matter as defined by claim 8, comprising from about 450 to about 600 mg ibuprofen and said adjuvant consisting essentially of from about 100 to about 150 mg caffeine.

* * * * *

UNITED STATES PATENT AND TRADEMARK OFFICE
CERTIFICATE OF CORRECTION

PATENT NO. : 4,420,483

DATED : December 13, 1983

INVENTOR(S) : ABRAHAM SUNSHINE et al

It is certified that error appears in the above-identified patent and that said Letters Patent is hereby corrected as shown below:

IN THE SPECIFICATION:

Column 1, line 46, kindly delete "and".

Column 7, line 60, after "65", kindly insert --mg--.

IN THE CLAIMS:

Claim 1, line 6, delete "pharmaceuticl" and kindly insert --pharmaceutical--.

Claim 1, line 9, delete "ibuprofen and" and kindly insert --an--.

Claim 8, line 8, delete "ibuprofen and" and kindly insert --an--.

Signed and Sealed this

Thirty-first Day of December 1985

[SEAL]

Attest:

DONALD J. QUIGG

Attesting Officer       Commissioner of Patents and Trademarks